(12) United States Patent
Hauger et al.

(10) Patent No.: US 11,534,202 B2
(45) Date of Patent: Dec. 27, 2022

(54) CANNULA

(71) Applicant: Pajunk GmbH Medizintechnologie, Geisingen (DE)

(72) Inventors: Martin Hauger, Donaueschingen (DE); Simone Pajunk-Schelling, Geisingen (DE)

(73) Assignee: Pajunk GmbH Medizintechnologie, Geisingen (DE)

( * ) Notice: Subject to any disclaimer, the term of this patent is extended or adjusted under 35 U.S.C. 154(b) by 587 days.

(21) Appl. No.: 16/556,839

(22) Filed: Aug. 30, 2019

(65) Prior Publication Data
US 2020/0078048 A1 Mar. 12, 2020

(30) Foreign Application Priority Data
Sep. 6, 2018 (DE) ...................... 10 2018 121 733.1

(51) Int. Cl.
*A61M 5/158* (2006.01)
*A61N 1/36* (2006.01)
*A61M 19/00* (2006.01)
*A61B 17/34* (2006.01)

(52) U.S. Cl.
CPC ......... *A61B 17/3421* (2013.01); *A61M 5/158* (2013.01); *A61N 1/36017* (2013.01); *A61B 2017/347* (2013.01); *A61M 19/00* (2013.01)

(58) Field of Classification Search
CPC .......... A61B 17/3421; A61B 2017/347; A61B 2017/00477; A61B 10/0283; A61M 5/158; A61M 19/00; A61M 1/774; A61M 5/16804; A61N 1/36017; A61N 1/05; A61N 1/36021; A61N 1/0502; A61N 1/0551
See application file for complete search history.

(56) References Cited

U.S. PATENT DOCUMENTS

| 5,098,430 A * | 3/1992 | Fleenor .............. A61B 18/1402 606/49 |
| 7,022,115 B1 | 4/2006 | Meier et al. |
| 2008/0200835 A1 | 8/2008 | Monson et al. |

(Continued)

FOREIGN PATENT DOCUMENTS

| CA | 3021629 | 12/2017 |
| DE | 102016110379 | 1/2017 |

(Continued)

OTHER PUBLICATIONS

German Patent and Trademark Office, "Office Action" issued in German Patent Application No. 10 2018 121 733.1, dated Jul. 15, 2019, document of 12 pages.

(Continued)

*Primary Examiner* — Bhisma Mehta
*Assistant Examiner* — Phoebe Anne Staton
(74) *Attorney, Agent, or Firm* — Akerman LLP; Peter A. Chiabotti

(57) ABSTRACT

The present application relates to a cannula, comprising a cannula body with a cannula tube and a body part attached to the proximal end of the cannula tube, a control clip having a mounting body with at least one control element, said control clip being attachable laterally on the body part to form a first configuration. In addition, the present applications relates to a cannula body, a contact clip and a control clip of a cannula.

19 Claims, 3 Drawing Sheets

(56) References Cited

U.S. PATENT DOCUMENTS

| | | | |
|---|---|---|---|
| 2009/0163860 A1* | 6/2009 | Patrick | G16H 20/17 |
| | | | 604/83 |
| 2009/0187222 A1 | 7/2009 | Barker | |
| 2010/0204568 A1 | 8/2010 | Narouze | |
| 2011/0046513 A1* | 2/2011 | Hibner | A61B 10/0275 |
| | | | 600/567 |
| 2012/0109007 A1* | 5/2012 | Rhad | A61B 10/0096 |
| | | | 600/567 |
| 2012/0116364 A1* | 5/2012 | Houser | H02J 7/0047 |
| | | | 606/1 |
| 2014/0025039 A1 | 1/2014 | Rajendran et al. | |
| 2015/0359999 A1 | 12/2015 | Khalaj | |

FOREIGN PATENT DOCUMENTS

| | | |
|---|---|---|
| DE | 102016110379 | 12/2017 |
| EP | 1002500 | 5/2000 |
| EP | 1611922 | 4/2006 |
| WO | 2010/012024 | 2/2010 |

OTHER PUBLICATIONS

European Pai Ent Office, "Search Report" from parallel European Patent Application No. 19 183 959.6, document of 6 pages, dated Dec. 18, 2019.

New Zealand Intellectual Property Office, "Office Action" issued in New Zealand patent Application No. 755981, dated Jan. 7, 2022, document of 5 pages.

New Zealand Intellectual Property Office, "Patent Examiner Report 2," dated Jun. 8, 2022, document of 5 pages.

Canadian Intellectual Property Office, "Office Action", dated Jun. 7, 2022, document for 4 pages.

European Patent Office "European Search Report," and English language translation thereof, dated May 20, 2022, document of 10 pages.

* cited by examiner

CANNULA

CROSS-REFERENCE TO RELATED APPLICATIONS

This application claims priority to German Patent Application No. 10 2018 121 733.1, filed Sep. 6, 2018, which is incorporated by reference in its entirety.

BACKGROUND

The present application relates to a cannula, a cannula body, a control clip, and a contact clip.

Cannulas in different configurations are well-known in the prior art. Cannulas typically comprise a cannula tube made of an electrically conductive material, preferably metal, with a body part disposed at the proximal end thereof and a cannula tip disposed at the distal end thereof. By means of the body part, the cannula tip can be fed transcutaneously to a nerve of a patient by medical personnel for treatment purposes, wherein the position of the cannula tip can be determined, inter alia, by electrical stimulation impulses. The electrical stimulation impulses are supplied via a stimulation cable which contacts the electrically conducting cannula tube in the region of a proximal body part of the cannula. Such cannulas are known, for example, from U.S. Pat. No. 7,022,115 B1, EP 1 002 500 A1 and DE 10 2016 110 379 A1 and are used in particular in anesthesia for peripheral nerve block.

In therapy or in anesthesia, ultrasound is used more and more to observe and check the exact position of the cannula tip and the cannula tube, respectively, in the patient to be treated. For this purpose, an ultrasound probe emitting ultrasonic signals and receiving the ultrasonic signals reflected by the metallic cannula tube is placed on the body surface of the patient. As a result of the improved ultrasound visibility of the cannula, as described, for example, in WO 2010/012 024 A1, the anesthetists are increasingly limited to the ultrasonic location of the cannula tube and dispense with the electrical stimulation.

It has proven disadvantageous that the medical personnel on the one hand must hold the ultrasound probe for checking and observing the position of the cannula tube and, in addition, on the one hand control the supply and aspiration of a liquid through the cannula, in particular a local anesthetic, by suitable control elements, and on the other hand must set the electrical stimulation impulses. In the cannulas known from the prior art, the operation has proven to be cumbersome and required increased staffing of medical personnel in the treatment of the patient.

The application discloses an improved cannula, which expediently eliminates the disadvantages known from the prior art cannulas and conveniently combines a simplified operation by medical personnel as well as cost advantages in the production and reuse of individual components. In particular, the handling of the improved cannula and the ultrasound probe for observing and checking the position of the cannula tube should be possible by a single person, wherein all functions of the cannula, that is to say controlling the supply of liquids and/or the removal of liquids or injecting and/or aspirating and providing stimulation impulses as well as the guiding of the cannula or the positioning of the distal end of the cannula tube at the nerve, can be done in a single operation. Combining stimulation and ultrasound aims at enabling more safety for patients and medical personnel. The pictorial sonographic representation of the individual anatomy of the patient and the simultaneous control of the spacing of the cannula and the nerve by means of stimulation not only allow an optimization of the puncture accuracy and thus an optimal effect and optimal use of the local anesthetic in terms of the amount used when injecting the local anesthetic, but, as a technique, provide also a proven time advantage in the treatment.

These objects are achieved by a cannula as disclosed herein. In addition, these objects are achieved by a cannula body, a control clip, and a contact clip as disclosed herein.

The application discloses embodiments of a cannula in the manner of a modular system in several parts, whereby this cannula, depending on the intended application, can be equipped in a first configuration with a control clip, or in a second configuration, additionally with a contact clip for electrical stimulation.

The cannula with the features and structures recited herein comprises a cannula body having a cannula tube and a body part attached to a proximal end of the cannula tube, and a control clip, having a mounting body with at least one electrical control element, said mounting body being laterally attachable to the body part to form a first configuration.

In a second configuration, the cannula can be provided with contact clip which is arranged ergonomically laterally on the body part. The contact clip comprises a mounting part with at least one electrical contact, wherein the contact clip is laterally attachable to the body part to form the second configuration, and the electrical contact in the second configuration establishes an electrical connection between a stimulation cable and an electrically conductive wire of the cannula tube in the region of the body part. In the second configuration, the cannula can be used for electrical stimulation in the manner of a conventional technique known from the prior art, wherein, preferably, the at least one control element of the contact clip can be used to control the electrical stimulation impulses in the second configuration. After use of the cannula, the contact clip can be removed from the body part and used for the treatment of other patients after appropriate cleaning.

According to a further advantageous embodiment, the mounting part of the contact clip has at least one pair of resilient latching arms which engage the body part. The mounting of the contact clip is thus effected by means of a latching connection, wherein the contact clip is attached laterally on the body part and the resilient latching arms each have at least one latching lug which engages a corresponding latching recess in the body part and/or engages behind a corresponding edge of the body part. When the contact clip is transferred to the body part for forming the second configuration, the latching arms rest diametrically to one another on both sides of the body part, the recess being in the region of the body part between the latching arms for engaging the electrical contact of the contact clip. Alternatively, the contact clip or the mounting part of the contact clip can be adapted to be pivotally mounted on the body part and locked at the body part by the resilient latching arms.

An advantageous development of the present application provides that, in the second configuration, the electrical contact engages a recess of the body part and electrically contacts the cannula tube. Thus, if the contact clip is attached to the body part by the mounting part for forming the second configuration the electrical contact engages the recess of the body part. The recess of the body part does not cover the metallic cannula tube or the electrically conducting wire of the non-electrically conductive cannula tube and allows an electrical connection between the electrical contact and the metallic cannula tube or the electrically conductive wire of the cannula tube. Accordingly, in the mounting part of the contact clip, the electrical contact is disposed on the body part-facing side, which does not affect the outer design of the body part, and the handling of the cannula is unobstructed and fully consistent with a conventional cannula known in the prior art.

It has proven advantageous if the electrical contact for electrically contacting the cannula tube is designed as an insulation displacement contact which is pressed onto the cannula tube during the transfer of the contact clip into the second configuration. The insulation displacement contact effects a reliable electrical contact with the cannula tube and ensures that no insulating layer on the cannula tube adversely affects the transmission of the electrical stimulation impulses from the electrical contact to the cannula tube or the electrically conducting wire of the cannula tube.

In addition, according to a further advantageous embodiment, the electrical contact is provided with a spring tab which is adapted to protrude into the recess of the body part and to rest on the cannula tube to form an electrical connection. In particular, it has proven advantageous if the free end of the spring tab is formed with sharp edges, whereby a secure electrical connection is effected when the spring tab rests on the cannula tube.

A further advantageous embodiment provides that the contact clip has a connector which can establish an electrically detachable connection to the stimulation cable. In particular, in this case, it has proven advantageous if the electrical contact has a further spring tab at a second end, which provides a clamping contact to form the electrical connector. As a result, a particularly compact connector is provided, which meets the requirements of a space-saving design. In this case it is particularly preferred that the connector is centrally located between the pairwise arranged latching arms and more preferably is held positively in the first and/or second configuration by retaining bars molded or joint at the body part.

According to a further advantageous embodiment, the at least one control element is an electrical control element. More preferably, the control element is connected to a control line, wherein the control line can be coupled to a device, which generates the electrical stimulation impulses which are transmitted to the electrically conducting wire of the cannula tube by means of the stimulation cable and the contact clip. In addition, more preferably, the control line can be electrically connected to the device or to a further device which is adapted to supply or aspirate a liquid which is to be injected or aspirated through the cannula tube. Accordingly, the at least one control element of the control clips is adapted to control an electrical current flowing in the stimulation cable which electrical current represents the stimulation impulses, in particular turning on and turning off. In addition, the at least one control element can be designed to control the stimulation impulses, in particular amplitude and frequency.

It is advantageous if the control clip has at least one second electrical control element, by means of which, for example, the liquid which is passed through the cannula tube and injected into the patient can be controlled. In particular, it is advantageous if the injection and/or the aspiration of the liquid can be switched on and off by the at least one second electrical control element. Furthermore, it may be advantageous, if the at least one second control element is adapted to have an effect on the injection—or aspiration rate, that is to say the amount of injected or aspirated liquid per unit time.

It is furthermore advantageous if the at least two latching arms of the mounting body of the control clip for mounting purposes laterally on the body part embrace the body part and/or the contact clip, and preferably establish a latching connection with the contact clip and/or the body part of the cannula. In this case, it is particularly advantageous if the at least two latching arms of the mounting body of the control clip are arranged diametrically spaced apart from one another and embrace the control clip and/or the body part. More preferably, in the first configuration, the contact clip is already located at the body part or in the region of the control clip between the at least two latching arms. This design measure for mounting the control clip affects the outer design of the body part or the cannula only slightly, making the handling of the cannula unobstructed and can be done in particular in one hand grip position with one hand. In particular, it is preferred if the at least two resilient latching arms of the control clip embrace the mounting part of the contact clip and the plug-in direction of the contact clip and the control clips is the same. Alternatively, the contact clip and the control clip may have different plug-in directions, wherein the plug-in directions are particularly preferably aligned rotated by 90°, 180° or 270° to one other around the cannula tube.

It is advantageous if the body part has a proximal connection, on which the liquid to be injected can be applied coaxially to the cannula tube. In particular, it is preferred that the connection is formed with an injection hose inserted in the body part. The injection hose is preferably fixedly disposed on the body part and is thus held without the risk of being lost. Through the connection, the liquid, in particular a local anesthetic can be introduced into the cannula tube to apply this liquid through the outlet opening at the cannula tip. The connection can be designed, for example, as a connector, in particular as a Luer-lock connector or as a NRfit connector. This connector may be formed directly on the body part or alternatively on the injection hose which is coaxially and sealingly attached to or in the body part.

According to a further advantageous embodiment, the at least one control element is embedded in the mounting body, whereby the at least one control element is fully hermetically protected in the fixing body against external influences, in particular liquids or contaminants. In particular, in doing so, a reuse of the control clip after an appropriate cleaning is possible.

Furthermore, it is particularly advantageous if the control element in the second configuration can be operated from the side facing away from the body part, which results in a particularly ergonomic handling of the cannula.

Also, it has proven advantageous if the mounting body has at least one deformable region, in particular at least one elastically deformable region, and that the at least one deformable region allows the at least one control element embedded in the mounting body to be operated. The operating movement of the medical personnel is transferred through the deformable region to the at least one control element, whereby this control element either generates a corresponding electrical switching signal or injection or aspiration is initiated mechanically.

In addition, according to an advantageous embodiment, the mounting body is made of at least one second electrically insulating plastic, which has a good deformability. Preferably, at least the at least one deformable region is made with the second electrically insulating plastic on the side facing away from the body part, whereby the electrical control element is particularly easy to operate. In particular, silicone-containing plastics have proven useful as the material for the second electrically insulating plastic.

It is advantageous if the control element can generate a haptically and/or optically and/or acoustically perceptible feedback. In particular, it is advantageous if the control element for generating a haptically and acoustically perceptible feedback has a snap dome and/or the control clip generates one or more visually perceptible signals, such as by lighting means, in particular LEDs.

Moreover, it is advantageous if the at least one control element is an electrically capacitive switch and/or an electrically inductive switch. Such switches are inexpensive and safe to use.

According to a further advantageous embodiment, the body part and/or the mounting part of the contact clip and/or the mounting body of the control clip is/are made of an electrically insulating plastic. In particular, it is advantageous if the body part, the mounting part and the mounting body are made in at least one one-component injection molding process.

Moreover, the present application relates to a cannula body, a contact clip and a control clip of a cannula. Thus, according to an embodiment, a cannula system is proposed which, in a first configuration, realizes an improved and simplified operation by means of a control clip attached laterally to the body part and, in a second configuration, enables stimulation by electrical currents.

BRIEF DESCRIPTION OF DRAWINGS

Hereinafter, with reference to the accompanying drawings, an exemplary and inventive embodiment will be explained in detail.

FIGS. 1 to 7 show an exemplary embodiment of a cannula.

DETAILED DESCRIPTION

Figure 1:
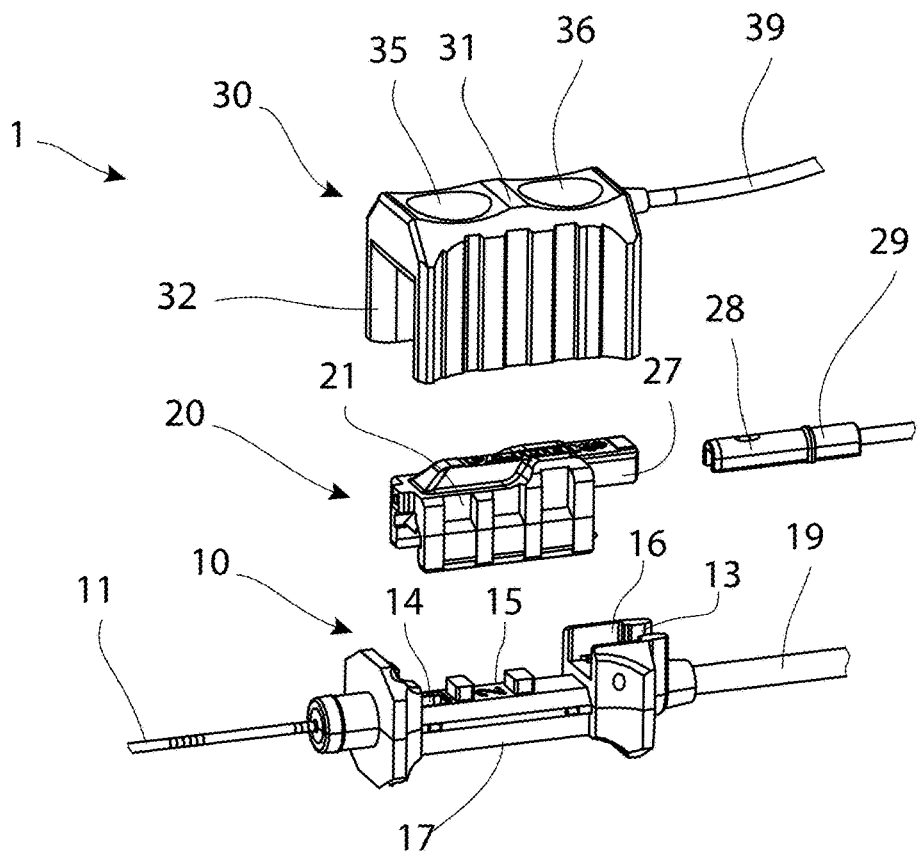
FIG. 1 shows an exploded perspective view of the cannula, having a cannula tube with a body part attached at the proximal end of the cannula tube, a contact clip and a control clip.

Cannula 1 comprises a cannula body with a cannula tube 11 extending coaxially along a longitudinal axis. Cannula tube 11 may be made of an electrically insulating material and may further have an electrically conductive wire. Alternatively, cannula tube 11 can be made of a metallic material and be coated on its outer circumference with an electrically insulating plastic.

Cannula tube 11 has a distal end and a proximal end, wherein a cannula tip (not shown) is formed at the distal end, which is adapted to be inserted in a patient's body for treatment purposes. At the proximal end of cannula tube 11, a body part 10 is arranged, which is preferably injection molded from an electrically insulating plastic material on cannula tube 11. The body part 10 has substantially the usual shape of a rectangular cuboid whose proximal and distal ends are widened in a flanged manner to allow a secure gripping and guiding of the cannula by medical personnel. An insertion recess 15 is formed between the flange at the distal end and the flange at the proximal end.

A connection 18 is arranged at the proximal end of body part 10. The connection 18 connects cannula tube 11 with injection hose 19—as can be seen in detail in FIG. 5. For this purpose, injection hose 19 is pushed over the proximal end, which protrudes from body part 10, and is attached or mounted fixedly and sealingly to body part 10.

Injection hose 19 is used for supplying and/or discharging a liquid, in particular a local anesthetic, which can be passed through cannula tube 11 to the cannula tip at the distal end and which can exit at the distal end of cannula 1. The injection hose may have a connection to its free end (not shown), e.g., a Luer lock connector or NRFit connector, to which a syringe or the like can be connected for supplying the liquid. Alternatively, the connector can also be formed directly on body part 10 or at connection 18 if no injection hose 19 is desired.

Figure 5:
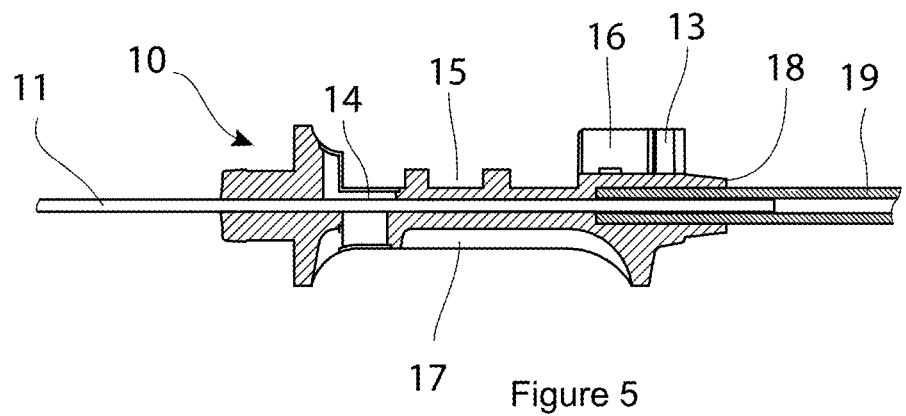
FIG. 5 shows a sectional view of the cannula tube with the body part attached to the proximal end.

As shown in FIGS. 1 and 5, body part 10 has a recess 14 in the region of insertion recess 15 between the distal flange and the proximal flange, which is open on the upper face, as shown in the drawing, of body part 10, and the depth of which extends at least to cannula tube 11. In the illustrated exemplary embodiment, recess 14 is open diametrically continuous through the body part 10.

Cannula tube 11 may be formed of plain metal in the region within recess 14, whereby metallic cannula tube 11 in this section has no insulating peripheral coating.

In addition, two cams projecting from cannula tube 11 are formed in the insertion recess 15, which are formed on the one hand spaced apart from the distal flange and recess 14, and on the other hand spaced apart from the proximal flange.

At the proximal end of body part 10 a notch 16 is incorporated in the proximal flange and which extends from insertion recess 15 to the proximal end continuously through the proximal flange and parallel to cannula tube 11.

Figure 6:
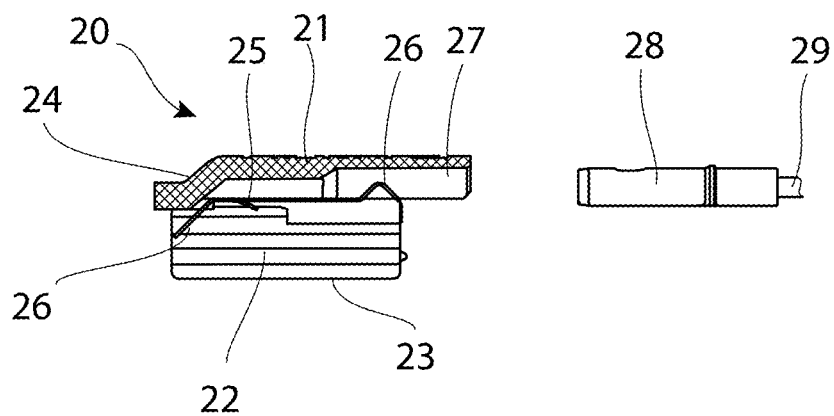
FIG. 6 shows a sectional view of the contact clip.
Figure 7:
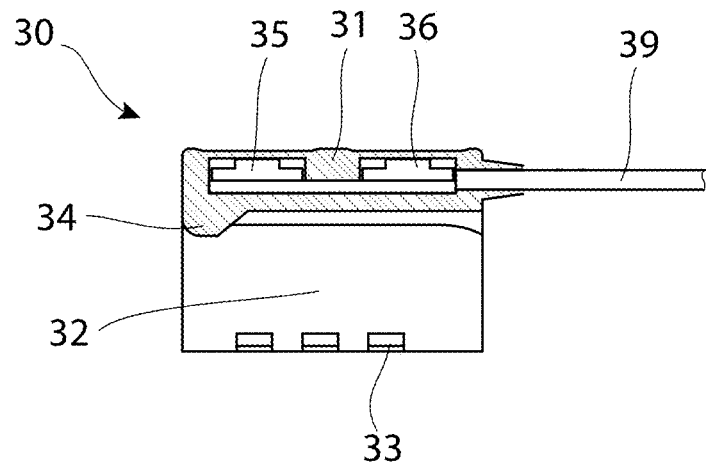
FIG. 7 shows a sectional view of the control clip.

In addition, cannula 1 comprises a contact clip 20 and a control clip 30, which is shown for example in FIG. 1 in a perspective view and in FIG. 6 in a sectional view.

Contact clip 20 comprises a mounting part 21 which is formed substantially in the form of a rectangular cuboid and in which a recess is formed or incorporated, which extends over the entire longitudinal extension from a proximal end to a distal end and forms two diametrically opposed latching arms 22. Accordingly, contact clip 20 is U-shaped in cross-section. Between the two pairwise arranged latching arms 22, an electrical contact 25 is arranged in recess of mounting part 21. Electrical contact 25 protrudes in the direction of the distal end of contact clip 20 into the recess between the two latching arms 22, wherein the free distal end of the electrical contact which projects into the recess, is formed as a spring tab 26 and can be deflected resiliently parallel to the two latching arms 22.

Furthermore, it can be seen in particular in FIG. 5 that the end of the electrical contact 25 facing the proximal end may also be formed as a spring tab 26 and projects in a free-standing manner in a region, which is designed as a connector 27. The free end of a mating connector 28 can be inserted into connector 27 to establish an electrical connection between a stimulation cable 29 and electrical contact 25. Mating connector 28 is held in connector 27, the spring tab 26 bearing against a mating electrical contact of mating connector 28 and contributes to the holding of mating connector 28 in connector 27 without the risk of being lost. The shape of connector 27 corresponds to the shape of the mating connector, wherein preferably the side of connector 27 facing body part 10 is open and is partially closed by electrical contact 25. Alternatively, stimulation cable 29 can also be attached directly to electrical contact 25.

At the respective free ends of latching arms 22 of mounting part 21 latching lugs 23 which are directed towards each other are formed on latching arms 22 which protrude into the recess.

In order to improve the handling of cannula 1, a control clip 30 can be plugged or clipped onto body part 10, thus forming a first configuration I. In the illustrated exemplary embodiment, however, it is provided that control clip 30 embraces contact clip 20 and body part 10 to form the first configuration I, contact clip 20 not being absolutely necessary for the realization of the first configuration I. In this case, control clip 30 is attached directly to body part 10.

Control clip 30 comprises a mounting body 31 and at least one control element 35, 36. In the illustrated exemplary embodiment control clip 30 comprises two electrical control elements 35, 36, however, the control elements may also be formed mechanically, for example as valves for controlling aspiration and application.

The first control element 35 and the second control element 36 can be operated independently of one another by the medical personnel, wherein the first control element 35 can be used for aspiration and the second control element 36 can be used for regulating or controlling the liquid to be injected. In addition, the first control element 35 and/or the second control element 36 can be used to control the electrical stimulation impulses.

In addition, control clip 30 may comprise a control line 39 which can be either detachably attached to control clip 30 by a plug connection, or is fixedly connected to control clip 30 and establishes an electrical connection to a unit, not shown, which effects, for example, aspiration or injection or generates the electrical stimulation impulses, which are passed through stimulation cable 29 to cannula tube 11 by means of electrical contact 25.

Control clip 30 has approximately the usual shape of a rectangular cuboid in which a recess extending from a proximal end to a distal end is incorporated or molded, whereby control clip 30 is U-shaped in cross-section. Through the recess, two diametrically aligned latching arms 32 are formed, at the free ends of which a plurality of latching lugs 33 are molded or joint, which, directed towards each other, project into the recess.

In mounting body 31, control elements 35, 36 are recessed, which means that control elements 35, 36 are hermetically surrounded by mounting body 31, which ensures that no liquids or contaminants can come into contact with control elements 35, 36.

Figure 4:
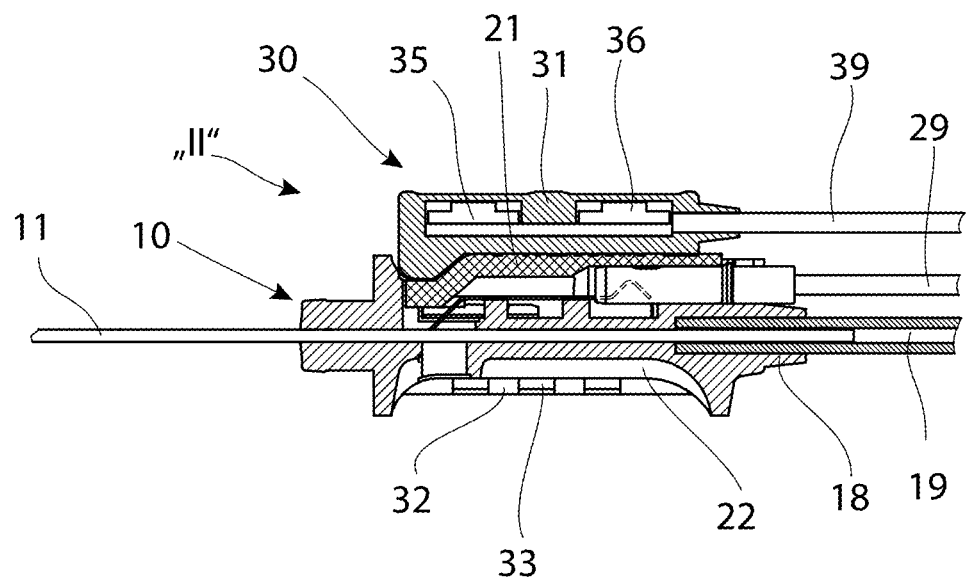
FIG. 4 shows a sectional view along a longitudinal axis through the cannula according to FIG. 3.

In FIGS. 1, 4, 6, control elements 35, 36 are arranged on the side of mounting body 31 facing away from cannula tube 11, and thus can be operated during the procedure with cannula 1 by the medical personnel with a first hand in one and the same hand-hold position while the same medical personnel holds the ultrasound probe with the second hand and observes and checks the position of the cannula during treatment, for example, anesthesia. Due to the easy handling of cannula 1, the medical personnel can devote full attention to this task.

In order to enable a simple and powerless operation of the control elements 35, 36, mounting body 31 is thin-walled in a region on the side facing away from cannula tube 11, whereby a mechanical operation by the medical personnel is transferred to control elements 35, 36 by a deformation of mounting body 31. In particular, it is preferred if the deformable region is made of a softer plastic, in particular silicone, whereby the mechanical resistance during operation is reduced and the handling is improved. It is particularly preferred to produce mounting body 31 in a two-component injection molding process.

In order for the medical personnel to devote full attention to the positioning of cannula tube 11 at the site of use, for example a nerve of the patient, when using cannula 1, an advantageous development provides that control elements 35, 36 upon operation generate a haptic, acoustic or visual feedback, wherein advantageously the haptic and acoustic feedback can be generated by a snap dome in the respective control element 35, 36.

If cannula 1 is to be used for the electrical stimulation, contact clip 20 can be attached to or clipped on body part 10, and contact clip 20 and the cannula body with body part 10 and cannula tube 11 together form the second configuration II. Contact clip 20 is attached in a plug-in direction perpendicular to cannula tube 11 on the body part.

Figure 2:
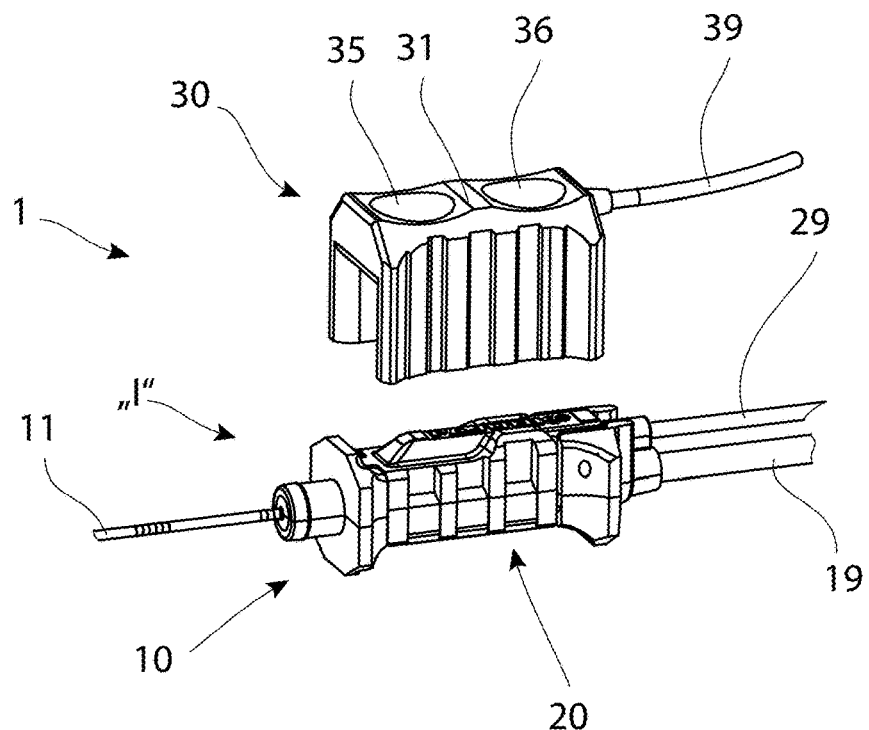
FIG. 2 shows a perspective view of the cannula according to FIG. 1, wherein the contact clip is attached to the body part.
Figure 3:
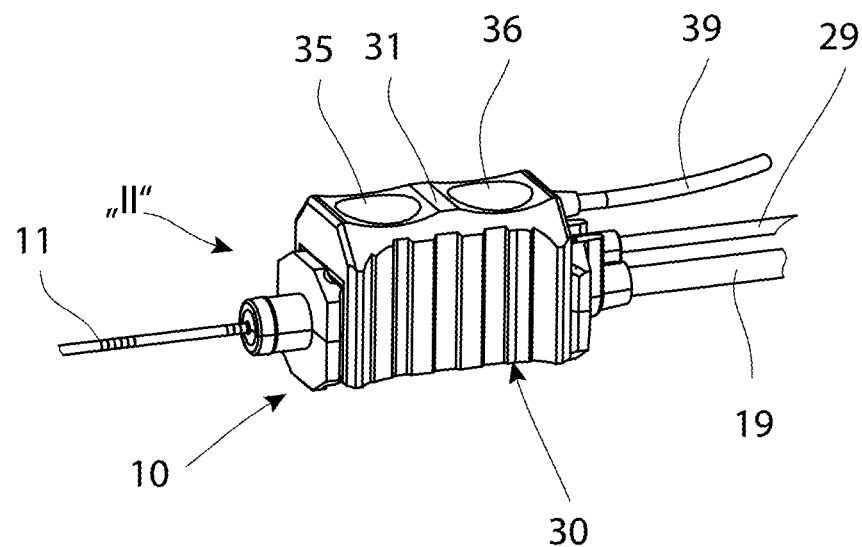
FIG. 3 shows a perspective view of the cannula according to FIG. 1 or 2, wherein said control clip is attached to the body part to form a first configuration.

The second configuration II is shown in perspective in FIG. 2 and it can be seen that in the second configuration I, contact clip 20 is inserted laterally in the plug-in direction in insertion recess 15 and the two latching arms 22 embrace body part 10 between the distal flange and the proximal flange, wherein latching lugs 23 engage body part 10 or an edge 17 on the side of body part 10 facing away from contact clip 20 partially from behind to form a positive snap or clip connection.

In the second configuration II, spring tab 26 of electrical contact 25 protrudes into recess 14 of body part 10 between the distal flange and the proximal flange and presses against cannula tube 11 with its spring tab 26 which is formed at the free end, whereby an electrical connection between electrical contact 25 and cannula tube 11 is accomplished.

Furthermore, the two cams arranged in insertion recess 15 press against electrical contact 25. Thereby, an additional clamping force on the second spring tab 26 at the proximal end of the contact clip 20 can be achieved, whereby the mating connector 28 is braced with connector 27 and detaching the electrical connection between stimulation cable 29 and electrical contact 25 is prevented. The proximal end of contact clip 20 is completely immersed in notch 16 at body part 10. In addition, two retaining bars 13 are formed in notch 16, which protrude from body part 10 into notch 16 and partially engage a bar at mating connector 28 and fix the mating connector in notch 16.

To transfer cannula 1 in first configuration I, control clip 30 is placed in the plug-in directions in the illustrated exemplary embodiment via second configuration I, or body part 10 and contact clip 20, wherein the two latching arms 32 embrace contact clip 20 diametrically and latching lugs 33 arranged on the free end of latching arms 32 are form-fitted with contact clip 20 by partially embracing contact clip 20 and the free end of latching arms 22 of contact clip 20, respectively. The position of control clip 30 between the distal flange and the proximal flange of body part 10 is fixed by the interaction of a depression 24 at the distal end of contact clip 20 and a protrusion 34 at the distal end of control clip 30 as well as at the distal flange on body part 10, which in the assembled state interlock in the first configuration I.

LIST OF REFERENCE NUMERALS 1 cannula
10 body part
11 cannula tube
13 retaining bar 14 recess
15 Insertion recess
16 notch
17 edge
18 connection
19 injection hose
20 contact clip
21 mounting part
22 latching arm
23 latching lug
24 depression
25 contact
26 spring tab
27 connector
28 mating connector
29 stimulation cables
30 control clip
31 mounting body
32 latching arm
33 latching lug
34 protrusion
35 control element
36 control element
39 control line

The invention claimed is:

1. A cannula, comprising:
   a cannula body having a cannula tube with a proximal end and a distal end;
   a body part attached to the proximal end of the cannula tube;
   a control clip having a mounting body with a control element, wherein the control clip is attachable laterally to the body part to form a first configuration;
   a contact clip with a mounting part having an electrical contact, wherein the contact clip is attachable to a side of the body part to form a second configuration wherein the control clip is located over the contact clip; and
   wherein the electrical contact in the second configuration establishes an electrical connection between a stimulation cable and the cannula tube.

2. The cannula according to claim 1, wherein the mounting part of the contact clip has a pair of resilient latching arms that embrace the body part for establishing a latching connection in the second configuration.

3. The cannula according to claim 1, wherein the electrical contact engages a recess of the body part and electrically contacts the cannula tube in the second configuration.

4. The cannula according to claim 3, wherein the electrical contact has a spring tab which rests on the cannula tube in the recess of the body part.

5. The cannula according to claim 1, wherein the electrical contact has an insulation displacement contact that is pressed onto the cannula tube.

6. The cannula according to claim 1, wherein the contact clip has a connector that can establish an electrically detachable connection to the stimulation cable.

7. The cannula according to claim 6, wherein the electrical contact has a spring tab for forming a clamping contact with the connector.

8. The cannula according to claim 1, wherein the control element is an electrical control element and connected with a control line.

9. The cannula according claim 1, wherein the control clip comprises at least two control elements.

10. The cannula according to claim 1, wherein the mounting body of the control clip comprises at least two latching arms embracing the body part and/or the mounting part of the contact clip.

11. The cannula according to claim 1, wherein a proximal connection for introducing a liquid is attached coaxially on the body part to the cannula tube.

12. The cannula according to claim 11, wherein the proximal connection is formed with an injection hose inserted in the body part.

13. The cannula according to claim 1, wherein the mounting body surrounds the control element, and wherein the control element is operable from a side facing away from the body part.

14. The cannula according claim 13, wherein the mounting body is deformable on the side facing away from the body part for operating the control element and/or the mounting body on the side facing away from the body part for operating the control element is made of a second electrically insulating plastic which is deformable.

15. The cannula according to claim 14, wherein upon operating the control element a haptic feedback is generated.

16. The cannula according to claim 15, wherein the control element comprises a plurality of control elements, wherein each control element of the plurality of control elements is an electrically capacitive switch or an electrically inductive switch.

17. The cannula according to claim 1, wherein the body part and/or the mounting part of the contact clip and/or the mounting body of the control clip are made of an electrically insulating plastic.

18. A device, comprising:
   a cannula;
   a body part located on the cannula;
   a contact clip that is detachably mountable to the body part to form a first configuration, wherein the contact clip comprises an electrical contact that establishes an electrical connection between a stimulation cable and the cannula; and
   a control clip that is detachably mountable to the body part over the contact clip to form a second configuration, wherein the control clip comprises a deformable body that is electrically insulated and at least two control elements.

19. The device according to claim 18, wherein the at least two control elements comprise a first control element that is depressable to control aspiration and a second control element that is depressable to control electrical stimulation impulses.

* * * * *